United States Patent [19]

Cox et al.

[11] Patent Number: 4,590,275

[45] Date of Patent: May 20, 1986

[54] BENZOHETERAZOLO[3,2-A]QUINOLINIUM SALTS

[75] Inventors: Osvaldo Cox, Guaynabo; Adriana Baez, San Juan, both of P.R.

[73] Assignee: Commonwealth of Puerto Rico, San Juan, P.R.

[21] Appl. No.: 504,880

[22] Filed: Jun. 16, 1983

Related U.S. Application Data

[63] Continuation-in-part of Ser. No. 357,696, Mar. 12, 1982, abandoned.

[51] Int. Cl.⁴ .................. C07D 471/04; C07D 517/04
[52] U.S. Cl. .......................................... 546/62; 546/41
[58] Field of Search .................................... 546/62, 41

[56] References Cited

U.S. PATENT DOCUMENTS 3,541,100 11/1970 Ramirez et al. .................. 546/62 X

OTHER PUBLICATIONS

Fozard, et al., J. Org. Chem., vol. 31, pp. 2346–2349, (1966).
Cox, et al., J. Med. Chem., vol. 25, No. 11, pp. 1378–1381, (11/82).
Cox, et al., 9th Annual Minority Biomedical Research Support Symposium, Sponsored by the Division of Research Resources, NIH, Albuquerque, N.M., Apr. 1981, Abstr. 483.
Bubnovskaya, et al., Chemical Abstracts, vol. 69, 11405m, (1968).

*Primary Examiner*—Nicholas S. Rizzo
*Assistant Examiner*—Diana G. Rivers
*Attorney, Agent, or Firm*—Scrivener Clarke Scrivener and Johnson

[57] ABSTRACT

The preparation of the hitherto unknown benzoheterazolo[3,2-a]quinolinium salts via, the photochemically induced cyclization of 2-chlorostyrylbenzoheterazoles is described. The new products show cytotoxic, antitumor and antiviral activity.

4 Claims, No Drawings

BENZOHETERAZOLO[3,2-A]QUINOLINIUM SALTS

RELATION TO OTHER CASES

This application is a continuation-in-part of our copending application Ser. No. 357,696; filed Mar. 12, 1982, now abandoned, for Synthesis And Biological Activity of Benzothiazolo(3,2-A), Benzoselenazolo(3,2-A) And Benzozazola(3,2-A)Quinolinium Salts.

SUMMARY OF THE INVENTION

It has now been unexpectedly and surprisingly found that benzoheterazolo[3,2-a][quinolinium salts] exhibit cytostatic and anti-tumor activity, and that these compounds can be prepared by photochemically induced cyclization of the corresponding 2-(2'-chlorostyryl)benzoheterazoles.

BACKGROUND OF THE INVENTION

The benzo[c]phenanthridine alkaloids fagaronine and nitidine represent a class of compounds isolated from the Rutaceae family that show potent antitumor activity against L1210 and P388 murine leukemias. Coralyne, a berbenium alkaloid structurally related to the benzo[c]phenanthridines, exhibits antitumor activity against both tumor screens. Studies on the mechanism of action of fagaronine an nitidine indicate that both alkaloids inhibit DNA synthesis is probably by interacting with A:T base pairs. Derivatives of these compounds have been described in *J. Med. Chem.*, 17, 347 (1974), ibid. 18, 66 (1975), ibid. 18, 708 (1975) and *J. Pharm. Sci.* 66, 1781 (1977) and shown to have antitumor activity.

In addition, *Proc. Natl. Acad. Sci U.S.A.*, 71, 5078 (1974) and *J. Med. Chem.* 23, 1330 (1980) report that the presence of a positive charge on the nitrogen atom helps to stabilize the complexes formed with DNA. It also is known by those skilled in the art that a variety of thiazole and fused thiazole derivatives also display biological activity, as reported in *Indian J. of Chem.*, 19B, 894 (1980) and *Indian J. Chem.* 11, 1115 (1973).

SUMMARY OF THE INVENTION

In accordance with the present invention compounds of formula I have been prepared.

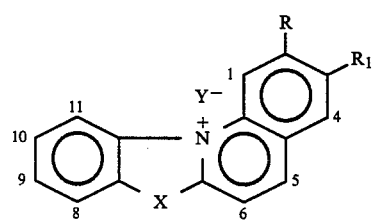

The synthetic sequence commences with the condensation of a 2-chloro-benzaldehyde with 2-methylbenzothiazole II in boiling acetic anhydride to give 2-(2'-chlorostyryl)benzothiazole III.

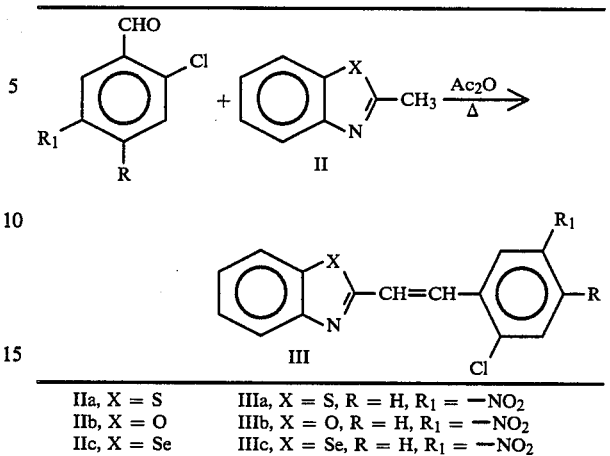

| | |
|---|---|
| IIa, X = S | IIIa, X = S, R = H, $R_1$ = $-NO_2$ |
| IIb, X = O | IIIb, X = O, R = H, $R_1$ = $-NO_2$ |
| IIc, X = Se | IIIc, X = Se, R = H, $R_1$ = $-NO_2$ |

Exposure of dilute solutions of III in a benzene-dioxane (3:1) solution to a Hanovia 450 W mercury arc lamp for 24 h, using an internally cooled Vycor vessel, resulted in the formation of benzothiazolo[3,2-a]quinolinium chloride 1.

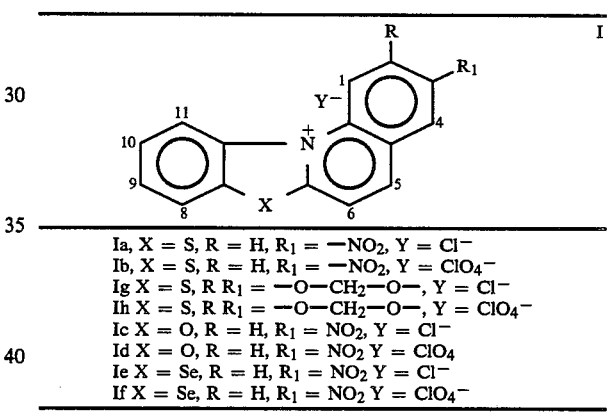

| | |
|---|---|
| Ia, X = S, R = H, $R_1$ = $-NO_2$, Y = $Cl^-$ |
| Ib, X = S, R = H, $R_1$ = $-NO_2$, Y = $ClO_4^-$ |
| Ig X = S, R $R_1$ = $-O-CH_2-O-$, Y = $Cl^-$ |
| Ih X = S, R $R_1$ = $-O-CH_2-O-$, Y = $ClO_4^-$ |
| Ic X = O, R = H, $R_1$ = $NO_2$, Y = $Cl^-$ |
| Id X = O, R = H, $R_1$ = $NO_2$ Y = $ClO_4$ |
| Ie X = Se, R = H, $R_1$ = $NO_2$ Y = $Cl^-$ |
| If X = Se, R = H, $R_1$ = $NO_2$ Y = $ClO_4^-$ |

The chlorides of formula I are very soluble in water, however, the corresponding perchlorates of formula I precipitate upon addition of 70% aqueous perchloric acid to the solution. Confirmation of the structures of I rests on satisfactory elemental composition by combustion analysis, $^1H$ NMR, $^{13}C$ NMR, IR and UV spectral data (see Experimental Section) of the corresponding perchlorates. Tables I and II summarize the physical and composition analysis of compounds Ib, d, f, h, j, and l, respectively.

Cytotoxic activities were tested by exposing HeLa and/or KB cells "in vitro" to compounds I. These results are summarized in Table III. Compound Ib displays the highest cytotoxicity against both screens. It appears that structural variations such as replacement of sulfur for oxygen or selenium as well as changes in the electronic nature of the substituents are critical factors in eliciting the inhibitory activity. Since in general satisfactory cytotoxic activity "in vitro" corresponds to good antitumor activity in vivo, the antitumor activity of compound Ib was assessed in mice bearing Ehrlich ascites tumor. A range of doses from 400 mg/kg to 90 mg/kg were tested, each given in a one dose basis, 24 h after tumor implantation. The most effective dose was 200 mg/kg, which gave a T/C value of −6.2. Mice that were given 400 and 300 mg/kg doses died within 24 h of injection presumabley from drug toxicity. Compound Ib was also tested against P388 leukemia in mice. The antitumor experiments are summarized in Table IV.

In addition, herpes simplex virus (HSV-1) infected KB cells and KB mock-infected cells were assayed for protein synthesis in the presence of Ib at different concentrations. These results indicate that at 0.5M Ib inhibited preferentially translation on infected cells, thus indicating that Ib acted on the virus infected cells producing a drastic reduction on virus yield (see Experimental).

DETAILED DESCRIPTION OF THE INVENTION

This invention is still further illustrated by the following examples, which are not to be construed in any way or manner as imposing limitations upon the scope thereof. On the contrary, it is to be clearly understood that resort may be had to various other embodiments, modifications and equivalents, thereof which readily suggest themselves to those skilled in the art without departing from the spirit of the present invention and/or the scope of the appended claims.

Experimental

Melting points were determined in a Thomas-Hoover or a Melt-Temp apparatus and are uncorrected. The $^1$H and $^{13}$C nuclear magnetic resonance spectra were recorded in a JEOL-FX-90Q NMR spectrometer. Chemical shifts are referenced to internal tetramethylsilane. Ultraviolet spectra were recorded in a Hitachi-Perkin Elmer 200 UV-visible spectrophotometer. Elemental analyses were performed by Galbraith Laboratories, Inc., Knowville, Tenn. Analysis indicated only by symbols of the elements means that anlytical results obtained for those elements were within ±0.4% of the theoretical values. Irradiations were conducted under an Argon atmosphere in a 450-w Hanovia mercury vapor lamp in a standard immersion well fitted with a Vycor filter.

SYNTHETIC PROCEDURES

Example 1

Synthesis of 2-(2'-chloro-5'-nitrostyryl)benzothiazole. General Procedure for 2-Styrylbenzoheterazoles A solution of 12.4 g (67 mmol) of 2-chloro-5-nitrobenzaldehyde and 10.0 g (67 mmol) of freshly distilled 2-methylbenzothiazole in 60 ml of acetic anhydride was refluxed for 5 h. The precipitated yellow solid was collected by filtration and recrystallized from toluene to afford 14.9 g (70%) of 2-(2'-chloro-5'-nitrostyryl)benzothiazole (IIIa); mp 188°–189° C., UV $\lambda_{max}^{EtOH}$ nm ($\epsilon$) 214(16808), 332.5(28445); $^1$H-NMR $\delta_{TMS}^{CDCl_3}$ (ppm) 8.58 (d, J=2.7 Hz, 1H), 8.16–7.26 (complex pattern, 8H); $^{13}$C—NMR$^{TMS}$ $\delta_{TMS}^{DMSO-d6}$ (ppm) 165.0, 154.0, 147.1, 140.2, 135.3, 134.9, 131.1, 130.7, 127.3, 126.7, 126.0, 124.0, 123.6, 121.6, 121.0; IR $\nu_{max}^{Kbr}$ (cm$^{-1}$) 1521.8, 1455.4, 1342.4, 1116.3, 1046.3, 951.3, 873.34, 826.1, 724.1, 737.4, 728.3. Anal. Calcd. for $C_{15}H_9CiN_2O_2$: C, 56.87, H, 2.86, N, 8.84; Found: C, 56.84; H, 2.86, N, 8.73.

Example 2

2-(2'-Chloro-5'-nitrostyryl)benzoxazole IIIe

Following the general procedure this compound was obtained in 30% yield from 2-chloro-5-nitrobenzalde-hyde and 2-methylbenzoxazole, mp 177–178 (recrystallized from dioxane); UV $\lambda_{max}^{EtOH}$ nm ($\epsilon$) 202(11156), 325(18945), $^1$H-NMR $\delta_{TMS}^{CDCl_3}$ (ppm) 8.58 (d, J=2.7 Hz, 1H), 8.22–7.12 (complex pattern, 8H)-$^{13}$C-NMR $\delta_{TMS}^{CDCl_3}$ (ppm) 161.5, 150.7, 147.1, 142.3, 140.5, 135.1, 132.7, 132.2, 126.1, 124.9, 124.4, 122.1, 120.5, 119.5, 110.6; $\nu_{max}^{KBr}$ (cm$^{-1}$) 1534.7, 1520.4, 1450.5, 1345.0, 1305.6, 1239.6, 1045.0, 958.5, 857.4, 822.2, 767.7, 754.1, 737.4. Anal. Calcd. for: $C_{15}H_9ClN_2O_3$: C, 59.91, H, 3.00, N, 9.32. Found: C, 59.68, H, 3.00, N., 9.29.

Example 3

2-(2'-Chloro-5'-nitrostyryl)benzoselenazole IIIf

This compound was prepared in a similar manner in 44% yield from 2-chloro-5-nitrobenzaldehyde and 2-methylbenzoselenazole, mp 201°–203° C., UV $\lambda_{max}^{EtOH}$ nm ($\epsilon$) 208(31164), 225(31164), 331(34291); $^1$H-NMR $\delta_{TMS}^{CDCl_3}$ (ppm) 8.61 (d, J=2.7 Hz, 1H), 8.20–7.26 (complex pattern, 8H); $^{13}$C-NMR $\delta_{TMS}^{CDCl_3}$ (ppm) 169.2, 146.9, 140.2, 135.1, 131.7, 131.1, 130.1, 128.8, 128.5, 126.7, 126.1, 125.1, 124.8, 124.0, 121.9; IR $\nu_{max}^{KBr}$ (cm$^{-1}$) 1643.4, 1604.3, 1565.8, 1517.9, 1481.0, 1460.6, 1384.3, 1342.7, 1282.2, 1243.8, 1130.7, 1115.4, 1090.0, 910.9, 829.2, 815.2. Anal. Calcd. for $C_{15}H_9ClN_2O_2Se$: C, 49.53, H, 2.50, N, 7.70. Found: C, 49.66, H, 2.55, N, 7.77.

Example 4

Synthesis of 3-Nitrobenzothiazolo(3,2-a)quinolinium Perchlorate. General Procedure for the Benzoheterazolo(3,2-a)quinolinium Perchlorates I A solution of 2.0 g (6.3 mmol) of 2-(2'-chloro-5'-nitrostyryl)benzothiazole (IIIa) in 400 ml of a 3:1 benzene:dioxane solution was exposed to a 450-W Hanovia mercury vapor lamp with a standard immersion well fitted with a Vycor filter. The solution was kept under Argon atmosphere throughout the irradiation period period of 24 h. The irradiation was stopped at 2 h intervals in order to remove the water soluble substance adhered to the insert. The aqueous solution was filterred and there was added 0.25 ml 70% perchloric acid. The precipitated solid was collected by filtration, washed several times and dried to afford 187 mg (9% yield) of Ib, mp 308°–309° C. (decomposition): $\lambda_{max}^{EtOH}$ nm ($\epsilon$) 206(23340), 272.5 (28,000) and 364 (15212); $^1$H-NMR $\delta_{TMS}^{DMSO-d6}$ (ppm) 9.59–7.47 (complex pattern); $^{13}$C-NMR $\delta_{TMS}^{DMS-d6}$ (ppm) 162.0, 145.7, 140.0, 139.0, 138.7, 129.7, 129.4, 127.3, 126.6, 125.5, 121.3, 121.1, 120.1; $\nu_{max}^{KBr}$ (cm$^{-1}$) 1607.3, 1538.9, 1349.2, 1087.9, 816.5, 764.7. Anal. Calcd. for $C_{15}H_9ClN_2O_6S$: C, 47.32, H, 2.36, N, 7.36. Found: C, 47.62, H, 2.65, N, 7.13.

Example 5

3-Nitrobenzoxazolo(3,2-a)quinolinium Perchlorate Ij

Following the general procedure, this compound was obtained from 2-(2'-chloro-5'-nitrostyryl)benzoxazole (Id) in 1% yield, mp 230° C.; $\lambda_{max}^{EtOH}$ nm ($\epsilon$) 223(29927), 258(29,187), 326(15,884) $^1$H-NMR $\delta_{TMS}^{DMSO-d6}$ (ppm) 8.78–6.88 (complex pattern); $^{13}$C-NMR $\delta_{TMS}^{DMSO-d6}$ 160.6, 153.0, 144.5, 141.5, 139.6, 130.3, 129.7, 124.8, 123.5, 120.9, 119.8, 119.4, 117.0, 115.9. Anal. Calcd. for $C_{15}H_9ClN_2O_7$: C, 49.36, H, 2.46, N, 7.67. Found: C, 49.66, H, 2.50, N, 7.34.

Example 6

3-Nitrobenzoselenazolo(3,2-a)quinolinium Perchlorate Il

Following general procedure, this compound was obtained from 2-(2'-chloro-5'-nitrostyryl)benzoselenazole (II) in 6.5% yield, mp 200° C. UV $\lambda_{max}^{EtOH}$ nm ($\epsilon$) 215(47488), 223(48121), 277(39889), 388(26592); $^1$H-NMR $\delta_{TMS}^{DMSO-d6}$ (ppm) 9.46–6.38 (complex pattern); $^{13}$C-NMR $\delta_{TMS}^{DMSO-d6}$ (ppm) 160.8, 143.7, 142.1, 140.4, 136.5, 134.8, 130.5, 130.2, 129.2, 125.0, 123.1, 119.6, 116.1; IR $\nu_{max}^{KBr}$ (cm$^{-1}$) 1621.5, 1602.6, 1502.5, 1354.2, 1129.3, 1096.9, 813.8, 771.1. Anal. Calcd. for $C_{15}H_9ClN_2O_6Se$: C, 42.11, H, 2.11, N, 6.55. Found: C, 42.26, H, 2.29, N, 6.24.

Example 7

Cytotoxicity Studies

HeLa-229 and KB cells were used for in vitro tissue culture cytotoxicity experiments. Cells were grown in monolayer culture in Difco TC Minimal Medium Eagle and supplemented with 10% foetal calf serum (Flow). Subculturing was performed every 6-7 days. Ehrlich ascites tumor was maintained in serial passages at two week intervals in Albino Swiss mice by intraperitoneal implant.

The method was essentially as described in Cancer Chemotherapy Rep. Part 3, 3, 2 (1972); NCI Monograph 45, p. 150. Drugs were always suspended in sterile 0.5% carboxymethyl cellulose. As a positive control 1 $\mu$M 6-mercaptopurine was always included. The results of these experiments are summarized in Table III.

Example 8

Antitumor Activity

The mice used through these experiments were female Albino Swiss mice.

Each group consisted of five to six weight matched animals. To begin the antitumor experiment $1 \times 10^6$ viable cells (trypan blue exclusion test) were injected ip. Test compounds were suspended in 0.9% (w/v) NaCl solution containing 0.10% (v/v) Tween 80 at the higher concentration. Lower doses were obtained by serial dilutions with 0.9% NaCl and injected ip in a volume of 0.5 ml in a single dose 24 h after implantation of the tumor. Animal body weights were recorded daily during the next 30 days and the survival was followed for the next 60 days. The P388 leukemia assay was performed according to standard protocol, Cancer Chemotherapy Rep.; Part 3, 3, 2 (1972); NCI Monograph 45, p. 150. These results are summarized in Table IV.

Example 9

Antiviral Activity

Screening of antibiotic action on protein synthesis in virus infected cells.

Herpes simplex virus (HSV-1) infected KB cells and KB mock-infected cells were assayed for protein synthesis in the presence of nitrobenzothiazolo quinolium perchlorate at different concentrations. After infection or mock-infection nitrobenzothiazolo quinolium perchlorate was added at the concentration of 100, 50, 25, 5 and 1.5 $\mu$g/ml and incubated for 48 hours.

After the incubation time, protein synthesis was measured by addition of 0.1 $\mu$Ci$^{35}$S methionine (1,100 Ci/mol; 5.4 mCl/ml) and incubated for 1 hour. After incubation the medium was removed, the reaction stopped and the radioactivity estimated in an Intertechnique liquid scintillation spectrometer.

The value 100% of control represents 72,484 cpm (mock-infected KB cells). Results obtained showed that a concentration of $5 \times 10^{-4}$M nitrobenzothiazolo quinolium perchlorate inhibited preferentially translation on infected cells, indicating that the inhibitor acted on the virus infected cell and produced a drastic reduction on virus yield.

TABLE I

| | | Composition Analysis of I$^a$ | | | | | |
|---|---|---|---|---|---|---|---|
| | | C, % | | H, % | | N, % | |
| Compound | Formula | Calcd. | Found | Calcd. | Found | Calcd. | Found |
| Ib | $C_{15}H_9ClN_2O_6S$ | 47.32 | 47.62 | 2.36 | 2.65 | 7.36 | 7.13 |
| j | $C_{15}H_9ClN_2O_7$ | 49.36 | 49.66 | 2.46 | 2.50 | 7.67 | 7.34 |
| l | $C_{15}H_9ClN_2O_6Se$ | 42.11 | 42.26 | 2.11 | 2.29 | 6.55 | 6.24 |
| d | $C_{15}H_{10}ClNO_4S$ | 53.65 | 54.04 | 2.98 | 3.34 | 4.17 | 3.99 |

TABLE II

| | | | | Some Physical and Spectral Properties of I | | | |
|---|---|---|---|---|---|---|---|
| Compound | X | R | R$_1$ | $\lambda_{max}^{EtOH}$ nm($\epsilon$) | $\nu_{max}^{KBr}$ cm$^{-1}$ | mp °C. | Yield (%) |
| Ib | S | H | NO$_2$ | 206(23340), 273(15426), 364(15212) | 1607, 1539 1349, 1087 817, 765 | 309 | 9 |
| Id | O | H | NO$_2$ | 223(29927), 240(29187) | | 230 | 1 |
| If | Se | H | NO$_2$ | 215(47488), 223(48121), 277(39889), 388(26592) | 1622, 1603 1503, 1354, 1129, 1097, 813, 771 | 200 | 6.5 |

TABLE III

| | Cytotoxic Activity[1] | |
|---|---|---|
| Compound | ED$_{50}$ $\mu$g/mL KB | ED$_{50}$ $\mu$g/mL HeLa |
| Ib | 0.61 | 0.9 |
| Ii | 12.0 | 15 |
| Il | 100.0 | — |

[1]Results are the average of at least three experiments.

TABLE IV

Antitumor Activity of Ib Against Ehrlich Ascites Tumor and P388 Leukemia in Mice.[a]

| Ehrlich ascites[b] | | | | | P388 leukemia[c] | | | |
|---|---|---|---|---|---|---|---|---|
| Dose[d] (mg/kg) | T/C[e] (%) | Survival | Toxicity[f] | LTS[g] | Dose[d] (mg/kg) | T/C[h] | Survival | Toxicity |
| 400 | | 0/6 | 6/6 | | 400 | | 0/6 | 6/6 |
| 250 | −2.5 | 6/6 | | 15/18 | | | | |
| 200 | −6.9 | 6/6 | | 18/18 | 200 | 218 | 6/6 | |
| 150 | −0.4 | 6/6 | | 15/18 | | | | |
| 100[i] | 35.8 | 6/6 | | 12/12 | | | | |
| 90[i] | 57.3 | 3/5 | | 5/10 | | | | |

[a]Average of three tests except when noted.
[b] and [c]Assay performed according to procols of NCI. 5-Fluorouracil was used as control (200 mg/kg/ing).
[d]Treatment given ip on Day 1.
[e]Significance response shows a T/C 42% at Day 12.
[f]Toxicity = LTS number of toxic deaths/number of treated mice.
[g]LTS = long term survivors (60 days)/number of treated mice.
[h]Median survival time of treated mice/median survival of control × 100. Values of T/C 120 denote activity.
[i]Ancrage of two test results.

We claim:

1. A compound selected from the group consisting benzoheterazol[3,2-a]quinolinium salts of formula 1,

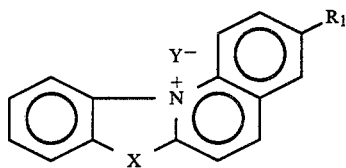

wherein $R_1$ is a nitro group and X is selected from the group consisting of oxygen, sulfur and selenium and $Y^-$ is a pharmaceutically acceptable anion.

2. A benzoheterazolo[3,2-a]quinolinium salt according to claim 1: 3-nitrobenzothiazolo[3,2-a]quinoliun chloride or perchlorate.

3. A benzoheterazolo[3,2-a]quinolinium salt according to claim 1: 3-nitrobenzoxazolo[3,2-a]quinolinium chloride or perchlorate.

4. A benzoheterazolo[3,2-a]quinolinium salt according to claim 1: 3-nitrobenzoselenazolo[3,2-a]quinolinium chloride or perchlorate.

* * * * *